United States Patent [19]
Graser et al.

[11] Patent Number: 6,027,622
[45] Date of Patent: Feb. 22, 2000

[54] SENSOR ELEMENT

[75] Inventors: Theodor Graser, Stuttgart; Hnas-Joerg Renz, Leinfelden-Echterdingen, both of Germany

[73] Assignee: Robert Bosch GmbH, Stuttgart, Germany

[21] Appl. No.: 09/080,834

[22] Filed: May 18, 1998

[30] Foreign Application Priority Data

May 17, 1997 [DE] Germany .................. 197 20 892

[51] Int. Cl.[7] .................. G01N 27/26; G01N 7/00
[52] U.S. Cl. ................ 204/426; 73/31.06; 438/68
[58] Field of Search ............... 73/35.06, 31.05, 73/31.06, 23.32; 204/425, 426; 438/68, 71

[56] References Cited

U.S. PATENT DOCUMENTS

| | | | |
|---|---|---|---|
| 4,574,264 | 3/1986 | Takahashi et al. ............ | 73/31.06 X |
| 4,604,161 | 8/1986 | Araghi ........................ | 438/68 |
| 4,851,371 | 7/1989 | Fisher et al. ................ | 438/21 |
| 5,345,213 | 9/1994 | Semancik et al. ............ | 338/34 |
| 5,445,920 | 8/1995 | Saito .......................... | 430/311 |
| 5,480,535 | 1/1996 | Kondo et al. ................ | 204/425 |
| 5,827,415 | 10/1998 | Gür et al. .................... | 204/426 |

*Primary Examiner*—Hezron Williams
*Assistant Examiner*—Jay L. Politzer
*Attorney, Agent, or Firm*—Kenyon & Kenyon

[57] ABSTRACT

A sensor element for an electrochemical sensor that determines the oxygen content of exhaust gases produced by internal combustion engines. The sensor element includes at least one measurement device and at least one heating device associated with the measurement device. The measurement device and the heating device both include individual functional layers laminated one above another. The heating device is covered with a surface layer that covers not only the surface of the outermost layer of the functional layers of the heating device, but also the side surfaces of all the functional layers of the heating device.

3 Claims, 1 Drawing Sheet

SENSOR ELEMENT

FIELD OF THE INVENTION

The present invention relates to a sensor element of an electrochemical sensor for determining the oxygen content of exhaust gases produced by an internal combustion engine.

BACKGROUND INFORMATION

Known sensor elements are configured, for example, as so-called planar sensors. These sensor elements include a solid electrolyte configured as a support, a measured gas electrode exposed to a measured gas, and, on the other side of the support, a reference gas electrode exposed to a reference gas. In a variety of applications, the sensor element must be heated to a specific temperature. It is known, for this purpose, to associate with the sensor element a heating device which usually has heating conductors extending in insulation layers beneath the electrode exposed to the reference gas.

To protect the electrode supply lead and the heater, it is known to equip the sensor element on both sides with a thick surface layer. The sensor elements are usually manufactured in batches by applying the individual functional layers of the sensor element in successive laminating processes (such as, for example, successive laminating silk screen printing processes) as areas and fine lines, and dicing into the individual sensor elements is then performed. The assemblage of films and layers yielding the sensor element is then sintered to produce a sensor element.

A disadvantage with the sensor elements discussed above is the fact that although it is possible, when the sensor elements are diced from the large-area assemblage of layers applied in film fashion, to cover the outermost layer by means of the surface layer, the end surfaces and edges of the functional layers that become exposed along the cut edges do not have the surface layer. When the sensor elements are used as intended, these end surfaces are thus exposed directly to the measured gas, which may, for example, correspond to the exhaust gas of an internal combustion engine. As a result, these uncovered end surfaces and edges offer an ideal surface for attack by the measured gas and by constituents contained in the measured gas. These can lead to decomposition of the exposed functional layers, and thus to an impairment of the characteristic curve of the sensor element.

SUMMARY OF THE INVENTION

The sensor element according to the present invention has the advantage that the functional layers of the heating device are coated by a surface layer on all sides exposed to the measured gas. Because the surface layer covers not only the surface of the outermost functional layer of the heating device but also the end surfaces of all the functional layers of the heating device, no opportunity exists for the measured gas and the constituents contained in the measured gas to attack the functional layers.

In a preferred embodiment of the present invention, provision is made for the surface layer fitting around the functional layers of the heating device to be applied by lamination, e.g., by means of a silk screen printing operation. As a result, no additional printing step is needed as compared with the production method of the known sensor element discussed above. In particular, provision is made in a preferred embodiment for the functional layers of the heating device to be configured with a lesser width as compared with the support layer for the heating device, so that gaps result between adjacent functional layers when the sensor elements are manufactured as an assemblage. These gaps are also filled up while the surface layer is being applied, thus resulting in additional edge protection. During subsequent dicing of the sensor elements, cutting takes place along these depressions so that the end surfaces and edges of the functional layers of the heating device are not uncovered by the dicing.

DETAILED DESCRIPTION

Figure 1:
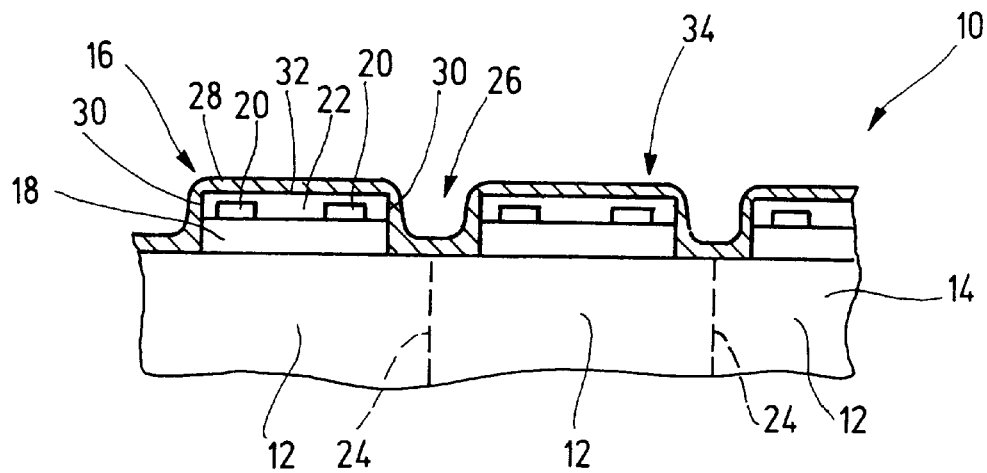
FIG. 1 shows a schematic cross-section of an assemblage of sensor elements according to the present invention.
Figure 2:
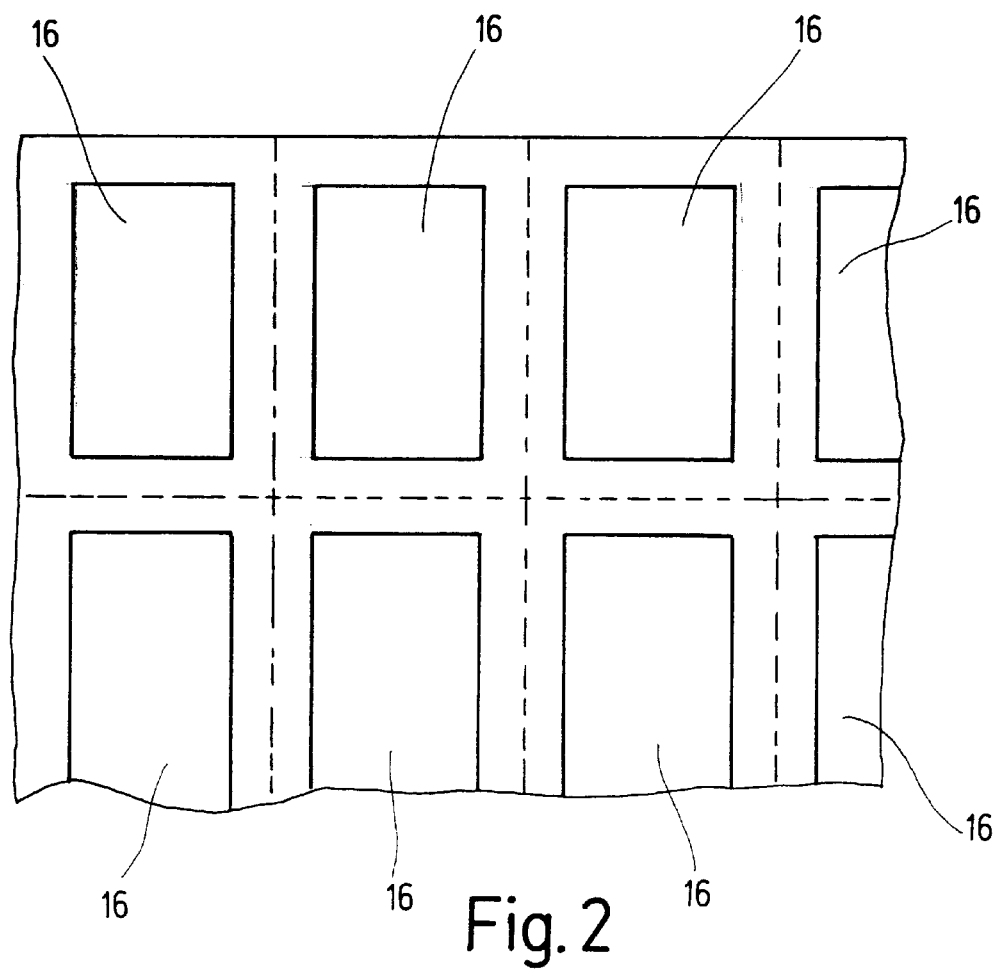
FIG. 2 shows a plan view of the assemblage of sensor elements according to the present invention.

FIG. 1 shows an assemblage 10 of multiple sensor elements 12. The depiction is only partial, i.e., assemblage 10 possesses in total a plurality of sensor elements 12 which can be accommodated on a corresponding substrate. In addition, the depiction of sensor elements 12 is not complete. Sensor elements 12 possess a measurement device (not depicted) which is arranged on a support 14, such that support 14 can be a component of the measurement device. The measurement device possesses the construction, known per se, in which a solid electrolyte has on the one side a reference gas electrode and on the other side a measured gas electrode. A heating device 16 is provided to heat the measurement device. Heating device 16 consists of a first insulation layer 18, heating conductors 20 arranged on first insulation layer 18, and a second insulation layer 22 surrounding heating conductors 20. The definition of heating device 16, i.e., of the individual functional layers of heating device 16, is accomplished by means of defined application of corresponding materials, generally by silk screen printing. The individual layers are applied as films onto support 14. Corresponding to the size of the entire substrate, a plurality of heating devices 16 is applied simultaneously, in a defined pattern, onto the measurement devices that are correspondingly pre-patterned on the other side of support 14. FIG. 2 shows in a partial plan view, a substrate having applied thereto the plurality of heating devices 16.

Cut lines 24, along which dicing of the individual sensor elements 12 is accomplished, are drawn in for illustration. It is evident in particular from FIG. 1 that the functional layers of heating device 16, i.e., first insulation layer 18 and second insulation layer 22, are each lesser in width than sensor element 12. This results in a trough-like depression 26 between two adjacent heating devices 16, which initially are still joined by means of the continuous support 14.

A surface layer 28, made for example of a sealing material, is applied onto heating device 16 patterned onto support 14. Surface layer 28 is also applied by silk screen printing. Since surface layer 28—and also the further layers of sensor element 12—is applied in the unsintered state onto the "green" film, the material of surface layer 28 can, because of its plasticity, penetrate into depressions 26 and thus enclose first insulation layer 18 and second insulation layer 22, including their respective side surfaces 30 as well. In order to illustrate the arrangement of surface layer 28, a greatly enlarged depiction is selected in FIG. 1. The height of first insulation layer 18 and the height of second insulation layer 22 arranged one above another is approximately 50 to 80 $\mu$m, so that the application of surface layer 28 onto the entire assemblage 10 of as-yet-unseparated sensor elements 12 leads to the creation of a sort of "mountain landscape." The selection of material for surface layer 28, which is preferably made of aluminum oxide $Al_2O_3$, causes heating device 16 (not only on the side facing support 14, but also on surface 32), second insulation layer 22, and the respective side surfaces 30 of first insulation layer 18 and second insulation layer 22 to be surrounded.

In a subsequent process step, dicing of sensor elements 12 is accomplished by means of a cutting operation along cut lines 24. During this cutting, surface layer 28 is cut through in the region of depressions 26, preventing any uncovering of side surfaces 30. After subsequent sintering of sensor elements 12, heating device 16 is covered by surface layer 28 which is formed as a cup-shaped sealing frame which prevents any direct contact between heating device 16 and the measured gas or substances contained in the measured gas.

The overall result is thus a sensor element 12 having particularly high characteristic shift down ("CSD") resistance, i.e., a breakdown of the Nernst voltage in an electrochemical oxygen sensor resistance, which can be manufactured without increased outlay as compared with the existing manufacturing process for sensor elements 12.

What is claimed is:

1. A method for manufacturing a plurality of sensor elements, comprising the steps of:

laminating onto each of a predetermined plurality of areas of a support layer a first layer;

laminating over each first layer a second layer, wherein, in each predetermined area, the first and second layers jointly form a heating device, each of the predetermined areas of the support layer covered by the first and second layers having a width that is less than a width of the support layer so that a depression is formed between adjacent heating devices;

coating each of the plurality of heating devices and the depressions formed therebetween with a surface layer;

performing a dicing operating in a region of each depression to separate a plurality of sensor elements from one another, each of the sensor elements including a heating device, a portion of the surface layer and a portion of the support layer; and sintering each one of the plurality of sensor elements.

2. The method according to claim 1, wherein the dicing operation is performed along an imaginary cut line disposed along each depression.

3. The method according to claim 1, wherein each of the heating devices includes an abutting surface in contact with the support layer and side surfaces not in contact with the support layer, the surface layer covering all side surfaces of each of the heating devices.

* * * * *